US008915901B2

United States Patent
Paz et al.

(10) Patent No.: US 8,915,901 B2
(45) Date of Patent: Dec. 23, 2014

(54) FASTENING AND CARRYING DEVICE FOR A DISPOSABLE ABSORBENT INCONTINENCE PAD

(75) Inventors: Rui Miguel Paz, Heidenheim (DE); Ruediger Kesselmeier, Herbrechtingen (DE); Enno Gause, Heidenheim (DE)

(73) Assignee: Paul Hartmann Aktiengesellschaft, Heidenheim (DE)

( * ) Notice: Subject to any disclaimer, the term of this patent is extended or adjusted under 35 U.S.C. 154(b) by 329 days.

(21) Appl. No.: 13/501,759

(22) PCT Filed: Oct. 5, 2010

(86) PCT No.: PCT/EP2010/006066
§ 371 (c)(1),
(2), (4) Date: Apr. 13, 2012

(87) PCT Pub. No.: WO2011/044995
PCT Pub. Date: Apr. 21, 2011

(65) Prior Publication Data
US 2012/0209237 A1 Aug. 16, 2012

(30) Foreign Application Priority Data
Oct. 15, 2009 (DE) .......................... 10 2009 049 463

(51) Int. Cl.
*A61F 13/15* (2006.01)
*A61F 13/20* (2006.01)
*A61F 13/70* (2006.01)
*A61F 13/505* (2006.01)
*A61F 13/66* (2006.01)

(52) U.S. Cl.
CPC ................ *A61F 13/70* (2013.01); *A61F 13/505* (2013.01); *A61F 13/66* (2013.01)
USPC .......................................... 604/395; 604/393

(58) Field of Classification Search
CPC ........ A61F 13/505; A61F 13/70; A61F 13/66
USPC .......... 604/392, 393, 394, 395, 396, 397, 398
See application file for complete search history.

(56) References Cited

U.S. PATENT DOCUMENTS

| 791,354 A | 5/1905 | Merkley |
| 1,475,895 A | 11/1923 | Stein |

(Continued)

FOREIGN PATENT DOCUMENTS

| CH | 88065 | 2/1921 |
| DE | 876 300 | 5/1953 |

(Continued)

*Primary Examiner* — Michele M Kidwell
(74) *Attorney, Agent, or Firm* — Paul Vincent

(57) ABSTRACT

A fastening and carrying device (2) for a disposable absorbent incontinence pad (4) has a belt (6) which is closed on itself in a detachable manner by means of belt closure elements (22), thus forming a continuous hip opening in the circumferential hip direction (8). The belt (6) has one flap section (32, 34) each proceeding from the back region (16) and the abdominal region (14) extending in a longitudinal direction in direction (38) on the crotch region of the user, having preferably mechanically acting closure elements (40, 42) on the side thereof facing the body, which interact in a detachably adhering manner with complementary, preferably mechanically acting, closure elements on the side of the incontinence pad (4) facing away from the body.

14 Claims, 2 Drawing Sheets

(56) References Cited

U.S. PATENT DOCUMENTS

| | | | |
|---|---|---|---|
| 1,830,528 A * | 11/1931 | Cohon | 450/103 |
| 1,833,690 A * | 11/1931 | Penners | 248/210 |
| 2,017,499 A | 10/1935 | Hower | |
| 2,538,758 A | 1/1951 | Bricmont | |
| 2,705,957 A | 7/1953 | Mauro | |
| 3,324,856 A * | 6/1967 | Young | 604/394 |
| 4,022,212 A | 5/1977 | Lovison | |
| 4,597,110 A * | 7/1986 | Smith et al. | 2/408 |
| 4,675,918 A * | 6/1987 | O'Brien | 2/402 |
| 4,802,469 A * | 2/1989 | Gollestani | 128/98.1 |
| 4,960,414 A * | 10/1990 | Meyer | 604/395 |
| 5,304,162 A * | 4/1994 | Kuen | 604/391 |
| H1674 H * | 8/1997 | Ames et al. | 604/389 |
| 6,306,121 B1 * | 10/2001 | Damaghi et al. | 604/385.03 |
| 6,730,188 B2 * | 5/2004 | Sanders | 156/256 |
| 7,211,072 B2 * | 5/2007 | Nawata et al. | 604/392 |
| 7,438,709 B2 * | 10/2008 | Karami et al. | 604/389 |
| 7,789,868 B2 * | 9/2010 | Tachibana | 604/385.23 |
| 7,815,620 B2 * | 10/2010 | Coates et al. | 604/392 |
| 8,430,858 B2 * | 4/2013 | Back | 604/395 |
| 2004/0186456 A1 | 9/2004 | Nawata | |
| 2004/0267225 A1 | 12/2004 | Gandemo | |
| 2006/0247599 A1 | 11/2006 | Mullen | |
| 2008/0045870 A1 | 2/2008 | Nozik | |
| 2014/0303589 A1 * | 10/2014 | Paz et al. | 604/395 |

FOREIGN PATENT DOCUMENTS

| | | |
|---|---|---|
| DE | 900 744 | 1/1954 |
| DE | 1 063 331 | 2/1961 |
| DE | 75 29 067 | 9/1976 |
| GB | 1 200 177 | 7/1970 |
| JP | 2006-051240 | 2/2006 |

* cited by examiner

FASTENING AND CARRYING DEVICE FOR A DISPOSABLE ABSORBENT INCONTINENCE PAD

This application is the national stage of PCT/EP2010/006066 filed on Oct. 5, 2010 and claims Paris Convention Priority of DE 10 2009 049 463.4 filed Oct. 15, 2009.

BACKGROUND OF THE INVENTION

The invention relates to a fastening and carrying device for a disposable absorbent incontinence pad, having a hip belt that can be closed detachably onto itself by means of belt closure elements and thus forming a continuous hip opening in the circumferential hip direction, to which belt the incontinence pad is detachably fixable, so that it can be worn in the crotch region of the user and after use removed from the hip belt again and discareded, the hip belt including a front abdominal region, a rear back region and a left and a right side region.

One such fastening and carrying device is known from WO 2004/069122 A1, for example. In this known fastening and carrying device, the hip belt is closed onto itself in the abdominal region. In side regions on the right and left between the abdominal region and the back region, the hip belt extends downward and there on each side forms a flaplike extension to which a relatively wide absorbent diaper unit can be fixed; closure elements provided for it for the purpose on both sides, front and rear, are fixed on the side of the absorbent diaper unit facing the body.

EP 0 700 278 B1 also shows a so-called belt diaper with a relatively narrow hip belt being closable outo itself, to the side of which facing away from the body an absorbent unit on the order of a diaper can be fixed.

The object of the present invention is to create a fastening and carrying device of the type defined at the outset which can also be used in conjunction with relatively small incontinence pads yet which nevertheless, in the state in which it has been put on the user, forms a configuration on the order of underpants.

SUMMARY OF THE INVENTION

With a fastening and carrying device of the aforementioned type as the point of departure, this object is attained in that beginning at the back region and the abdominal region, the hip belt has one flap section each, provided preferably symmetrically to a longitudinal center axis and extending in a longitudinal direction in the direction toward the crotch region of the user; which flap section, on its body facing side, has preferably mechanically acting closure elements, which cooperate detachably adherently with complementary preferably mechanically acting closure elements on the side of the incontinence pad facing away from the body.

By means of the flap section extending in the direction of the crotch region of the user, the hip belt simultaneously forms the basic configuration of a pair of underpants, which to complete the form of the underpants needs only to be supplemented with a crotch region. In the fastening and carrying device of the invention, this crotch region is formed by the absorbent incontinence pad, and the applicable back and front flap section cooperates detachably adherently with the side of the incontinence pad facing away from the body, specifically by using preferably mechanically or adhesively acting closure elements.

To improve the fit and for easy manipulation, it proves advantageous if the applicable flap section tapers in the direction toward the crotch region.

It also proves advantageous if the closure elements of the flap section are provided on an end of the flap section toward the crotch. Moreover, on the rear and/or front flap section, one or more further closure elements may be provided, which are positioned between the end toward the crotch and the hip belt and which serve the purpose of additionally fixing the incontinence pad.

It also proves advantageous if the preferably mechanically acting closure elements of the flap section, in particular on the end of the flap section toward the crotch, are provided on a striplike material section which extends transversely to the longitudinal direction and is joined to the flap section. In this way, the flap section, over its entire two-dimensional extent in the transverse direction can be fixed detachably on the outer side of the incontinence pad in an intended way that is symmetrical for the user. Thus the flap section, can be spread out correctly and largely without creases and fixed, in a manner that as mentioned is adjusted to the user relative to the legs and the crotch region or to a longitudinal center axis.

The outer side of the incontinence pad should be embodied such that it corresponds with the closure elements of the flap section; that is, in the case of a mechanical closure element in the form of hooks, the outer side of the incontinence pad is preferably formed by a loop-forming component, preferably a nonwoven, in particular the nonwoven layer of a nonwoven-and-film laminate, while in the case of an adhesive closure element, the outer side of the incontinence pad is preferably formed by a film layer to which the adhesive closure elements can stick.

In a further concept of the invention, it proves advantageous if the closure elements of the flap section, in particular on the end toward the crotch, before being put to use, are folded onto the body facing side, of the flap section and in this configuration adhere, in an easily detachable way, to the body facing side, of the flap section. In this way, the closure elements provided on the flap section and in particular acting mechanically are deactivated, as long as they are not needed for fixing the incontinence pad, while the hip belt is being put on, especially onto persons who cannot care for themselves. The closure elements accordingly are not a hindrance to putting on the hip belt, by catching firmly on the hip belt or other components, such as bedsheets, pads placed beneath the patient, or the like. Specifically, in practice it can prove advantageous if the front and/or rear flap section is folded onto itself and/or onto the hip belt, and the fold is not opened up, in order to fix the pad, until the hip belt and the incontinence pad have been put on.

With a view to practical manipulability, it also proves advantageous if the hip belt can be opened and closed in only one region, and if in this region the belt closure elements are provided on free end sections of the hip belt. Hence the hip belt is elongated and has two end sections which can be closed onto one another by means of the belt closure elements, in order to make it possible to put the hip belt on the user around the circumference of the user's body.

In a refinement of this concept of the invention, it proves advantageous if in the other side region, in which the belt accordingly cannot be opened and closed, secondary closure elements are provided, by means of which a circumferential length of the hip belt is adjustable and thus at least the front flap section can be positioned symmetrically to the user's crotch. Preferably, the secondary closure elements are embodied such that when the fastening and carrying device has been put on, they are indistinguishable by sight and/or by touch from the belt closure elements. However, it can also prove advantageous if the secondary closure elements can be distinguished by sight and/or by touch from the belt closure elements, in order to indicate the different function of the closure elements. This can be done for instance by means of different colors, shapes, texture, or in other ways. The belt closure elements and the secondary closure elements are advantageously provided on both sides of the abdominal region and/or in side regions of the hip belt. When the hip belt is being put on a patient who is lying down, the caretaker passes the open, elongated hip belt underneath the patient's body at the level of the patient's hip or back. Then, in order to form the closed hip opening, the belt is closed onto itself by means of the belt closure elements. In this state, although the belt has been put on, it has not yet been brought into its optimal fitting shape, which is done by activating the secondary closure elements. For example, in this state, the flap section on the abdominal side is pulled toward the correct side by the pull in the circumferential hip direction that is exerted by the closing of the belt closure elements. This can be done by adjusting the optimal circumferential length of the hip and by suitable tension in the circumferential hip direction, by correspondingly optimally adjusting the secondary closure elements. Thus by means of these secondary closure elements—as already mentioned—it is not two open ends that are closed onto one another, but instead the circumferential length of the hip belt is adjusted as needed.

The secondary closure elements can be achieved in various ways. In one preferred embodiment of the invention, it is proposed that one component of the secondary closure elements is provided on a material section joined to the hip belt, and the other component is provided on an outer side of the hip belt itself. In such a way, the hip belt itself is not altered; instead, it is given an additional element in the form of the material section that has the secondary closure elements and that can be attached in an arbitrary way to the material of the hip belt, for instance by being sewn, glued, sealed, or ultrasonically welded to it, or by similar joining methods.

It also proves to be advantageous if the belt closure elements and/or the secondary closure elements extend over essentially the entire length of the hip belt in the longitudinal direction, or in other words the entire width of the hip belt. In this way, upon adjusting the secondary closure elements, a uniform pull on the belt can be exerted over the entire width of the belt.

It is also conceivable that the belt closure elements and/or the secondary closure elements taper or narrow toward their free end, to minimize friction of the corners of these closure elements with the user's skin.

To shorten the circumferential length of the belt by using the secondary closure elements, a Z-shaped fold of the belt is preferably done by closing the secondary closure elements and is maintained by the resultant pressure of the hip belt against the surfaces of the user's body and/or by friction of the portions of the Z-shaped fold that are in contact with one another.

With a view to creating a good fit and great wearing comfort, it proves advantageous if the hip belt includes at least one elastic section, preferably one elastic section in each side region, so that the hip belt is elastically stretchable in the circumferential hip direction.

It moreover proves advantageous if in the abdominal region and/or in the back region, the hip belt is embodied as essentially unstretchable.

In an alternative embodiment, however, it can also prove advantageous if one or more elastic portions are located in the abdominal region and/or the back region, preferably in the form of a wedge-shaped, trapezoidal or square elasticized area.

In terms of the dimensioning of the hip belt, it proves advantageous if the hip belt, preferably at each point, has an extension in the longitudinal direction of at least 5 cm, in particular at least 6 cm, in particular at least 7 cm, in particular at least 8 cm, in particular at least 9 cm, and more particularly at least 10 cm. This means the dimension of the hip belt in the longitudinal direction; that is, the width of the belt transversely to its circumferential length, specifically outside the front or rear flap section. The extension in the longitudinal direction is preferably 20 cm at most. Especially preferably, the extension in the abdominal region is less than in the back region, and the upper edge of the hip belt is preferably slightly contoured, to form an abdominal part that improves the fit of the product.

In terms of the dimensioning of the flap section, it proves advantageous if the flap section has an extension in the longitudinal direction over a circumferential edge, near the crotch, of the hip belt of at least 5 cm, in particular at least 6 cm, in particular at least 7 cm, in particular at least 8 cm, in particular at least 9 cm, in particular at least 10 cm, in particular at most 20 cm, in particular 10-18 cm, in particular 10-15 cm, and the front and rear flap sections can have the same extension or different lengths.

In a preferred embodiment of the invention, the applicable flap section is embodied in one piece with the abdominal region and/or with the back region of the hip belt. Separately attached flap sections of the same material as the hip belt or a different material from the hip belt are likewise conceivable.

The abdominal region and/or the back region of the hip belt is formed by a nonwoven material or a composite nonwoven material, in particular by an essentially unstretchable nonwoven material or composite nonwoven material.

Furthermore, it proves especially advantageous if an elastically stretchable side region of the hip belt is connected nondetachably to an essentially unstretchable abdominal region and to an essentially unstretchable back region. Preferably, each side region has an elastically stretchable section.

It moreover proves advantageous if the front and/or rear flap section is embodied in colored fashion; preferably the sections are colored differently, to serve as a visual aid in putting on the garment.

It is also advantageous if a marking is made on the front and/or rear flap section, which marking serves as a positioning aid for the incontinence pad, in such a way that if the incontinence pad and fastening and carrying device are put on correctly, the marking on the front and/or rear flap section is brought into alignment with a marking, for instance in the form of a wetness indicator, that is visible on the outer layer of the incontinence pad.

Further features, details and advantages of the invention will become apparent from the appended claims and from the drawings and the ensuing description of a preferred embodiment of the fastening and carrying device on the invention for a disposable absorbent incontinence pad.

In the drawings:

DESCRIPTION OF THE PREFERRED EMBODIMENT

Figure 1:
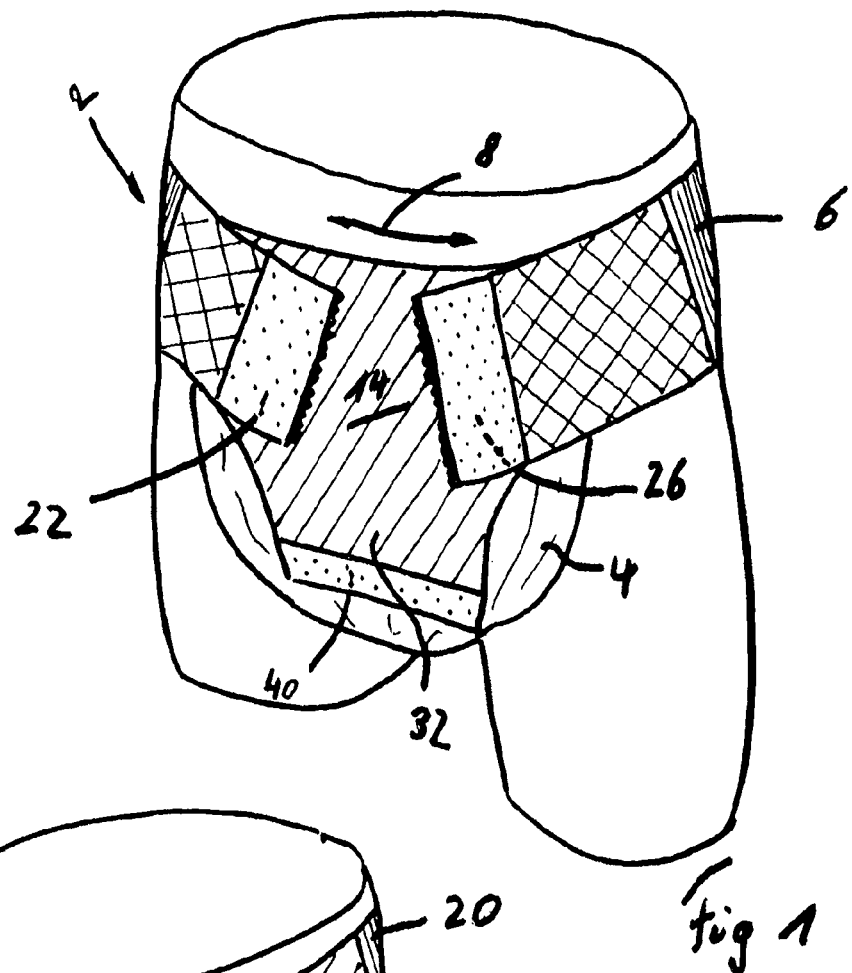
FIGS. 1 and 2 show an embodiment of the fastening and carrying device of the invention in the put-on state, together with a disposable absorbent incontinence pad.
Figure 2:
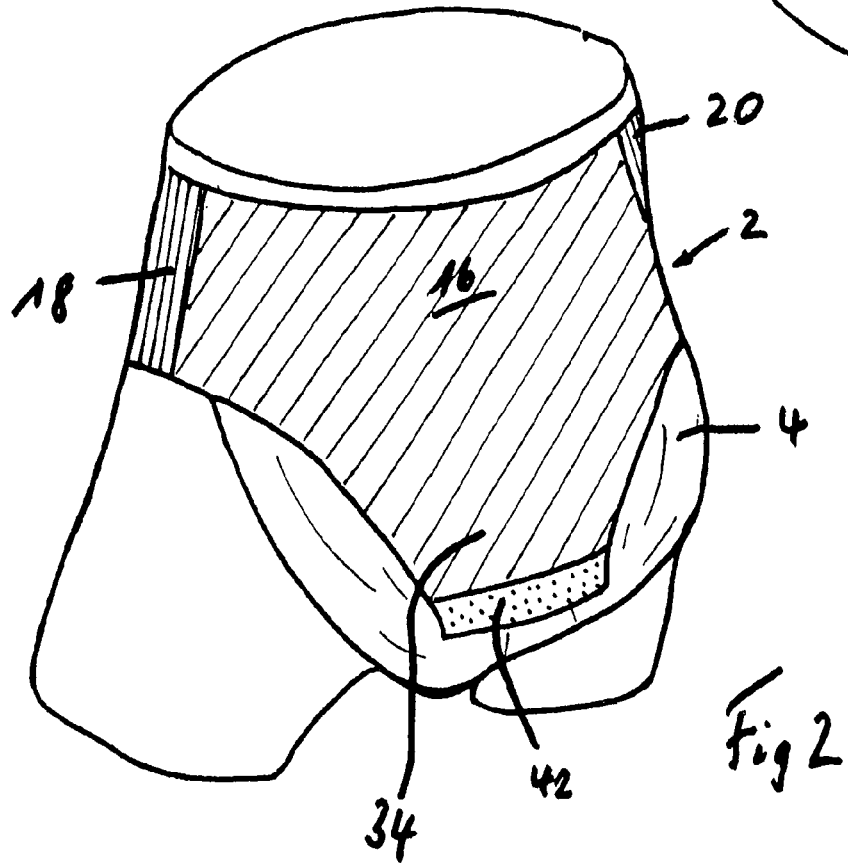
Figure 3:
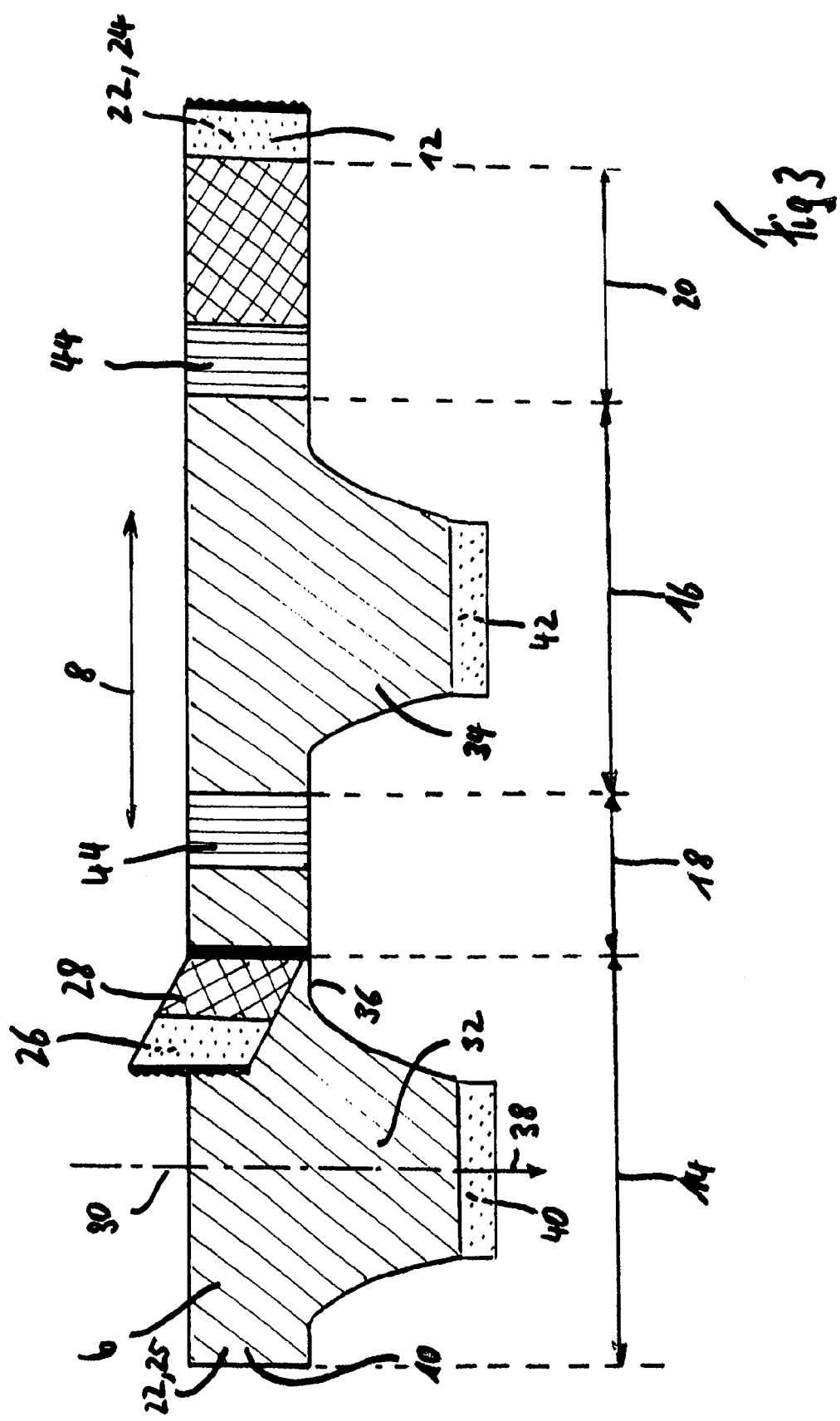
FIG. 3 is a schematic top view on the fastening and carrying device in the open state, spread out over a flat pad placed under the patient.

FIGS. 1 and 2 show perspective views of a fastening and carrying device, identified as a whole by reference numeral 2, for an absorbent incontinence pad identified by reference numeral 4, specifically in the state in which is has been put on a user. The fastening and carrying device 2 includes a hip belt 6 which can be closed detachably onto itself, and which extends along a circumferential hip direction 8 and has two free end sections 10, 12 (see FIG. 3), which are closable onto themselves to form the closed shape over the hip circumference.

The fastening and carrying device 2 and its hip belt 6 include a front abdominal region 14, a rear back region 16, and a left side region 18 and a right side region 20.

For closing the hip belt 6, belt closure elements 22 on its free end sections 10, 12 are provided, which in the preferred case shown as an example are formed by mechanically acting closure elements in the form of a hook-and-loop closure system. In the drawings, the hooklike closure component is shown at reference numeral 24; it cooperates detachably adherently with a loop-forming component 25 in the form of the outer surface of the abdominal region 14. For example, the outer side of the abdominal region 14 has a nonwoven material, which forms the looplike component 25 of the closure system.

Furthermore, the hip belt 6, which can be opened only at its end sections 10, 12, or in other words at only one point, has secondary closure elements 26, by means of which the circumferential length of the hip belt 6 can be adjusted. The secondary closure elements 26 are provided laterally in the abdominal region 14 and in the left side region 18 in such a way that when the fastening and carrying device has been put on (see FIG. 1), they lend the same visual impression as the belt closure elements 22 in terms of their embodiment and disposition, although their function is different. Specifically, by means of the secondary closure elements 26, no end sections of the hip belt 6 that can be opened and separated from one another are connected to one another; instead, the secondary closure elements 26 serve solely to adapt the circumferential length of the hip belt to the situation in which the garment is worn. For that purpose, the secondary closure elements 26 include a material section 28 which is attached to the outer side of the hip belt 6 on or at which the secondary closure elements themselves are provided. This material section 28 preferably extends over the entire longitudinal extension of the belt (along a longitudinal center axis 30), hence the entire belt width, to make it possible to introduce tensile forces uniformly into the hip belt. The secondary closure elements 26 are in turn preferably mechanically acting closure elements, in particular hook-and-loop materials. In the preferred exemplary case shown, the secondary closure elements 26 are embodied such that a hook-forming component of the closure system is provided on the material section 28 and cooperates with a loop-forming outer side of the abdominal region 14, in the manner described above for the belt closure elements 22.

As a further essential component, the hip belt 6 includes one front and one rear flap section 32, 34, beginning at the abdominal region 14 and the back region 16, respectively, and embodied symmetrically to a longitudinal center axis 30. The flap sections 32, 34, in the exemplary case shown, are embodied in one piece with the hip belt 6; they extend from a lower or crotch side longitudinal edge 36, of the hip belt in the direction 38 toward the crotch region along the longitudinal center axis 30. They can be contoured in a curved fashion laterally. In their lower end region toward the crotch, the flap sections 32, 34 include mechanically acting closure element 40, 42, specifically on the body facing side. These mechanically acting closure elements 40, 42 cooperate detachably adherently with complementary mechanically acting closure elements on the side of the incontinence pad 4 facing away from the body, in order to fix the incontinence pad 4 detachably, yet securely against being lost, to the fastening and carrying device 2. Preferably, the closure elements 40, 42 are the hook-forming component of a mechanically acting closure system, which component cooperates with the loop-forming component on the side of the incontinence pad 4 facing away from the body. The loop-forming component can advantageously be formed by a nonwoven coating, preferably the nonwoven ply of a nonwoven-and-film laminate, of the incontinence pad 4.

The hip belt 6 is preferably made from nonwoven or composite nonwoven materials. In the exemplary but preferred case shown, the abdominal region 14 and the back region 16 are formed from an essentially unstretchable nonwoven material or nonwoven composite material, whose outer side serves as the loop-forming component of the belt closure elements 22 or secondary closure elements 26. Conversely, the two side regions 18, 20 are embodied as elastically stretchable, in that they have an elastically stretchable material section 44, which as intended is connected nondetachably to the unstretchable material of which the abdominal region 14 and the back region 16 are made.

The fastening and carrying device 2 is put on, together with the absorbent incontinence pad 4, as follows: First, for a bedridden patient who cannot care for himself, the hip belt 6 is passed by a caregiver underneath the body of the patient at the level of the hip. In the process the hip belt 6 is positioned such that the back region 16 comes to rest under the patient's bottom and the abdominal region 14 comes to rest approximately at the center front. Then the free end sections 10, 12 of the hip belt 6 are positioned one above the other and are closed onto one another by means of the belt closure elements 22. By the ensuing positioning and closing of the material section 28 and the secondary closure elements 26, the length and tension of the hip belt 6 in the circumferential direction 8 are optimized, so that a uniform pull to the left and right is exerted on the abdominal region 14, and both the abdominal region 14 and the back region 16 preferably come to be located symmetrically relative to the patient and with as few creases as possible. The goal is also to make the garment feel comfortable when worn. Next, the front and rear flap section 32, 34, with the incontinence pad 4 either beforehand or only now positioned in the patient's crotch region, is connected detachably adherently, using the mechanically acting closure elements 40, 42. Here as well, care must be taken that the front and rear flap sections 32, 34 be fixed to the incontinence pad 4 by exerting a uniform and moderate tensile or holding force, so that the incontinence pad 4 stays in its intended symmetrical disposition in the patient's crotch region.

The caregiver is relatively free in terms of the order in which the steps described above are performed in putting the hygienic article or incontinence pad on. For instance, in some care situations, it can prove advantageous to preposition the incontinence pad in the crotch region of the patient first, and only then to close the hip belt 6 onto itself. It can also prove practical for the secondary closure elements 26 to be used only after the flap sections 32, 34 have been connected to the incontinence pad 4, in order to predetermine the optimal tension in the circumferential hip direction 8.

We claim:

1. A fastening and carrying device for a disposable absorbent incontinence pad, the incontinence pad being detachably attached to the fastening and carrying device for wear in a crotch region of a body of a user and for removal and disposal after use, the fastening and carrying device comprising:
    a front abdominal region, said front abdominal region having an upper portion defining a first hip belt region and a front flap section, said front flap section being one-piece-integral with said first hip belt region and extending in a longitudinal direction, downwardly from said first hip belt region towards the crotch region;
    a first side region undetachably adjoined to a right side of said first hip belt region to form a second hip belt region;
    secondary closure elements attached to an outer side of said front abdominal region or of said second hip belt region facing away from the body, thereby forming a flap or tab material section having a free end;
    a rear back region, said rear back region having an upper portion defining a third hip belt region and having a rear flap section, said rear flap section being one-piece-integral with said third hip belt region and extending in a longitudinal direction, downwardly from said third hip belt region towards the crotch region, said third hip belt region undetachably adjoined to a right side of said second hip belt region;
    a second side region undetachably adjoined to a right side of said third hip belt region to form a fourth hip belt region,
    wherein said first, second, third and fourth hip belt regions constitute a hip belt, which can only be opened between said first and said fourth hip belt regions;
    belt closure elements attached to a free end of said fourth hip belt region;
    a rear closure element attached to said rear flap section at a body-facing side thereof; and
    a front closure element attached to said front flap section at a body-facing side thereof, wherein said rear and front closure elements are structured to cooperate, in a detachable and adherent manner, with complementary closure elements on a side of the incontinence pad facing away from the body, the fastening and carrying device thereby being disposed, structured and dimensioned in such a manner that, when worn by the user, said belt closure elements and said secondary closure elements are disposed and closed onto a respective left and right side of the front abdominal region of the user, with said secondary closure elements adjusting a circumferential length of said hip belt to symmetrically position at least said front flap section with respect to the crotch of the user, wherein said belt closure elements detachably close said hip belt onto itself, thereby forming a continuous hip opening in a circumferential hip direction.

2. The fastening and carrying device of claim 1, wherein at least one of said front and said rear flap sections tapers towards the crotch region.

3. The fastening and carrying device of claim 1, wherein said front and rear closure elements are disposed on an end of a respective front and rear flap section facing the crotch.

4. The fastening and carrying device of claim 1, wherein said front and rear closure elements are disposed on a striplike material section, which extends transversely to the longitudinal direction and is joined to a respective said front and said rear flap section.

5. The fastening and carrying device of claim 1, wherein, prior to use of the device, said front and said rear closure elements are folded onto a body facing side of a respective said front and said rear flap section or said hip belt and, in this configuration, adhere, in an easily detachable way, to a body facing side of said respective flap section or said hip belt.

6. The fastening and carrying device of claim 1, wherein, as viewed in a put-on state of the fastening and carrying device, said secondary closure elements are visually and/or haptically indistinguishable from said belt closure elements.

7. The fastening and carrying device of claim 1, wherein, as viewed in a put-on state of the fastening and carrying device, said secondary closure elements are distinguished visually and/or haptically from said belt closure elements.

8. The fastening and carrying device of claim 1, wherein said belt closure elements and/or said secondary closure elements substantially extend over an entire length of said hip belt in the longitudinal direction.

9. The fastening and carrying device of claim 1, wherein said hip belt has at least one elastic section in a side region, said hip belt being elastically stretchable in a circumferential hip direction.

10. The fastening and carrying device of claim 1, wherein, in the abdominal and/or back region, said hip belt is substantially unstretchable.

11. The fastening and carrying device of ciaim 1, wherein said hip belt has an extension in a longitudinal direction of at least 5 cm.

12. The fastening and carrying device of claim 1, wherein at least one of said front and said rear flap section has an extension in the longitudinal direction past a circumferential edge near the crotch of said hip belt of at least 5 cm.

13. The fastening and carrying device of claim 1, wherein the abdominal and/or back region of said hip belt is made from a nonwoven material or a composite nonwoven material.

14. The fastening and carrying device of claim 1, wherein an elastically stretchable side region of said hip belt is connected nondetachably to a substantially unstretchable abdominal region and to a substantially unstretchable back region.

* * * * *